United States Patent [19]

Fischer et al.

[11] 4,410,719
[45] Oct. 18, 1983

[54] PREPARATION OF 2-ALKYL-4,4-DIACYLOXYBUT-2-ENALS

[75] Inventors: Rolf Fischer, Heidelberg; Hans-Martin Weitz, Bad Durkheim; Joachim Paust, Neuhofen, all of Fed. Rep. of Germany

[73] Assignee: BASF Aktiengesellschaft, Fed. Rep. of Germany

[21] Appl. No.: 393,499

[22] Filed: Jun. 29, 1982

[30] Foreign Application Priority Data

Jul. 1, 1981 [DE] Fed. Rep. of Germany ........ 3125891

[51] Int. Cl.³ .................... C07C 67/29; C07C 67/297; C07C 69/025; C07C 69/145
[52] U.S. Cl. ................................... 560/112; 560/113; 560/231; 560/234; 560/261; 560/262; 560/121; 560/128; 260/410.9 N; 260/405.6; 568/484
[58] Field of Search .............. 560/112, 113, 121, 128, 560/231, 234, 261, 262; 260/410.9 N, 401.6

[56] References Cited

FOREIGN PATENT DOCUMENTS 9752 5/1981 European Pat. Off. .
2357752 5/1975 Fed. Rep. of Germany .
2357810 5/1975 Fed. Rep. of Germany .
2225612 1/1976 Fed. Rep. of Germany .
2513999 10/1976 Fed. Rep. of Germany .

Primary Examiner—Paul J. Killos
Attorney, Agent, or Firm—Keil & Witherspoon

[57] ABSTRACT

2-Alkyl-4,4-diacyloxybut-2-enals of the formula

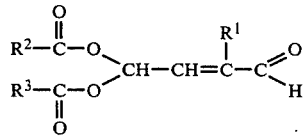

I where $R^1$ is alkyl and $R^2$ and $R^3$ are each hydrogen or an aliphatic, cycloaliphatic or aromatic radical, are prepared by a process in which a 2-alkyl-1,4-diacyloxybuta-1,3-diene of the formula

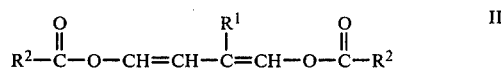

II is reacted with oxygen or an oxygen donor, in the presence of a carboxylic acid of the formula $R^3$-COOH

III.

3 Claims, No Drawings

PREPARATION OF 2-ALKYL-4,4-DIACYLOXYBUT-2-ENALS

The present invention relates to a process for the preparation of 2-alkyl-4,4-diacyloxybut-2-enals (2-alkyl-fumardialdehyde-4-monoacylals) by reacting a 2-alkyl-1,4-diacyloxybuta-1,3-diene with oxygen or an oxygen donor, in the presence of a carboxylic acid.

2-Alkylfumardialdehyde-4-monoacetals and 4-monoacylals are useful building blocks for the synthesis of various terpenes which exhibit biological and pharmacological activity. Several processes have been proposed for their preparation. Thus, German Laid-Open Applications DOS Nos. 2,357,752 and 2,357,810 disclose that 3-methylbut-2-en-1-al-acetals and the corresponding acylals can be oxidized with selenium dioxide to give trans-2-methylbut-2-ene-1,4-dial-4-acetals and the corresponding acylals. Using the process described in German Laid-Open Application DOS No. 2,225,612, cyclic 3-methylbut-2-en-4-ol-1-al-acetals can be oxidized with a chromic acid solution containing sulfuric acid to give the corresponding 2-methylbut-2-ene-1,4-dial-4-monoacetals.

It is also possible to prepare trans-2-methylbut-2-ene-1,4-dial-4-acetals as described in German Laid-Open Application DOS No. 2,513,999, by a multi-stage process in which, in a first step, crotonaldehyde-acetal is subjected to ozonolysis. European Patent 9,752 describes the reaction of six-membered cyclic acetals of 3-methylbut-3-en-1-al with nitrosating agents, such as nitrosyl chloride or nitrites, in the presence of methanol and hydrochloric acid. Using a base, hydrogen chloride is split off from the 2-chloro-2-methylbutane-1,4-dial-bisacetal formed, and the resulting 2-methylbut-2-ene-1,4-dialbisacetal can be hydrolyzed selectively, using a dilute aqueous acid, to give 2-methylfumarodialdehyde-4-monoacetal.

We have found that 2-alkyl-4,4-diacyloxybut-2-enals of the formula

where $R^1$ is alkyl of 1 to 5 carbon atoms and $R^2$ and $R^3$ are each hydrogen, an aliphatic radical of 1 to 15 carbon atoms, a cycloaliphatic radical of 5 to 7 carbon atoms or an aromatic radical, are obtained in a particularly advantageous manner when a 2-alkyl-1,4-diacyloxybuta-1,3-diene of the formula

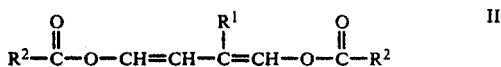

where $R^1$ and $R^2$ have the above meanings, is reacted with oxygen or an oxygen donor in the presence of a carboxylic acid of the formula $$R^3-COOH \qquad III$$

where $R^3$ has the above meanings.

Using the novel process, the 2-alkyl-1,4-diacyloxybuta-1,3-dienes can be converted to the 2-alkyl-4,4-diacyloxybut-2-enals in a reaction step which is technically simple to carry out, the products being obtained with high selectivity, predominantly as the trans-isomers.

In the preparation of 2-methyl-4,4-diacetoxybut-2-enal, the reaction may be presented formally by the following equation:

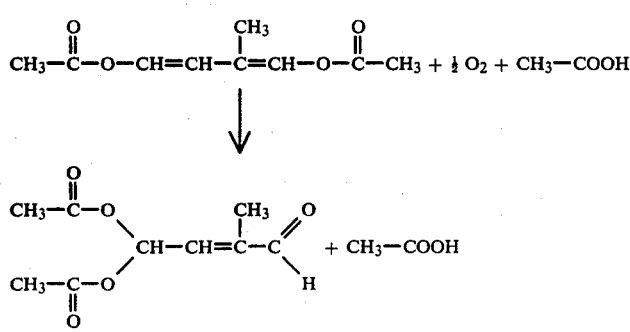

It is not necessary to isolate the intermediates in this reaction.

In the 2-alkyl-1,4-diacyloxybuta-1,3-dienes of the formula II which are used as starting materials, $R^1$ is alkyl of 1 to 5, preferably 1 to 3, carbon atoms, and the two radicals $R^2$ may be identical or different and are each hydrogen, an aliphatic radical of 1 to 15 carbon atoms, a cycloaliphatic radical of 5 to 7 carbon atoms or an aromatic radical. An aliphatic radical is, for example, alkyl, such as methyl, ethyl, n-propyl, i-propyl, n-butyl, i-butyl, tert.-butyl, n-pentyl, palmityl or stearyl.

Cycloaliphatic radicals are, for example, cyclopentyl, cyclohexyl and cycloheptyl. Aromatic radicals are, for example, unsubstituted phenyl and phenyl which is substituted by alkyl or halogen.

Examples of compounds of the formula II are 2-methyl-, 2-ethyl-, 2-n-propyl-, 2-butyl- and 2-pentyl-1,4-diacetoxybuta-1,3-diene, 2-methyl-1-propionyloxy-4-acetoxybuta-1,3-diene, 2-methyl-1-acetoxy-4-palmityloxybuta-1,3-diene, 2-methyl-1-cyclohexyloxy-4-acetoxybuta-1,3-diene and 2-methyl-1-benzoyloxy-4-acetoxybuta-1,3-diene.

The starting materials of the formula II can be prepared by, for example, acetylation of a 2-alkyl-4-acyloxybut-2-enal with acetic anhydride (J. Org. Chem. 41 (1976), 2625) or by the pyrolysis of a 2-alkyl-3,4-diacetoxy-tricyclo[4,2,1,0²,⁵]non-7-ene (J. Chem. Soc., Chemical Communications 1974, pages 956–957).

In the carboxylic acids of the formula III, $R^3$ has the meanings given for $R^2$, but $R^2$ and $R^3$ may be identical or different. Examples of carboxylic acids of the formula III are formic acid, acetic acid, propionic acid, butyric acid, valeric acid, capric acid, lauric acid, oleic acid, palmitic acid, cyclohexanecarboxylic acid, benzoic acid and phenylacetic acid, acetic acid being particularly preferred for economic reasons. The carboxylic acid is in general employed in excess, for example in an amount of from 1 to 80 moles per mole of the 1,3-diene II employed.

Oxygen can be used in the form of pure oxygen or as a mixture with other gases, such as nitrogen, for example as air, or with other inert gases, e.g. carbon dioxide.

Examples of suitable oxygen donors are those which are used for the epoxidation of olefins, examples being hydrogen peroxide, peracids, such as performic acid, peracetic acid, perpropionic acid, perbenzoic acid, per-n-butyric acid and per-iso-butyric acid, and organic hydroperoxides, such as tert.-butyl hydroperoxide and cumene hydroperoxide. Compounds of this type are mentioned in, for example, Ullmanns Encyclopädie der Technischen Chemie, 4th edition, volume 10, pages 563–567. The oxygen and the oxygen donor can also be employed in the presence of a catalyst. Particularly when a peracid is used, the reaction may also be carried out without the addition of a carboxylic acid of the formula III.

In the novel process, for example, from 1 to 80 moles, in particular from 1.5 to 60 moles, of the carboxylic acid III and from 0.5 to 10 moles, in particular from 1 to 1.5 moles, of oxygen or of the oxygen donor are employed per mole of the 1,3-diene II. The reaction is advantageously carried out at from 0° to 200° C., in particular from 20° to 120° C., under an oxygen pressure of, for example, from 1 to 100 bar, in particular from 1 to 20 bar.

The process can be carried out batchwise or continuously, under atmospheric or superatmospheric pressure. Unreacted 1,3-diene II can, if necessary, be separated off by distillation from the resulting 2-alkyl-4,4-diacyloxybut-2-enal I after the reaction and reused for the reaction according to the invention.

Usually, the reaction is carried out either in an excess of the carboxylic acid III as the solvent or in the presence of a solvent which is inert under the reaction conditions. Examples of solvents of this type are carboxylates, such as methyl acetate, chlorohydrocarbons, such as methylene chloride, chloroform, carbon tetrachloride and 1,2-dichloroethane, hydrocarbons, such as alkanes, benzene and alkylbenzenes, and ethers, such as diethyl ether, tetrahydrofuran and dioxane. Advantageously from 0.1 to 80 moles, in particular from 2 to 60 moles, of the above solvent are used per mole of starting compound II.

In a batchwise procedure, the reaction may, for example, be carried out as follows: oxygen or the oxygen donor is fed, at the reaction temperature and pressure, to a solution of the 1,3-diene II in the carboxyic acid III, in the presence or absence of a solvent, and, if necessary, the solution is further stirred after the addition is complete. If required, nitrogen is passed through the reaction mixture which has been cooled to room temperature. The solvent and/or the carboxylic acid III are distilled off, after which the mixture is fractionally distilled to separate off any unreacted starting compound from the desired aldehyde.

The 2-alkyl-4,4-diacyloxybut-2-enals I obtainable with high selectivity by the novel process are useful intermediates for the preparation of terpenes, such as retinal, β-carotin (German Laid-Open Application DOS. No. 2,357,810) and apocarotinoids.

Compared to the above conventional processes in which other starting materials are oxidized, the process according to the invention has the great advantage that oxygen or oxygen donors, such as hydrogen peroxide, percarboxylic acids or organic hydroperoxides, can be used instead of expensive and/or toxic oxidizing agents, such as selenium dioxide, chromic acid, ozone, nitrosyl chloride or nitrites.

The process of the invention is also surprising because it could not be foreseen that 2-alkyl-4,4-diacyloxybut-2-enals would be formed under the reaction conditions, and that these would be obtained very predominantly as the trans-isomers. European Patent 5,452 discloses, in fact, that a 2-alkyl-1,1,4,4-tetraacyloxybut-2-ene is formed in the reaction of a 2-alkyl-1,4-diacyloxybuta-1,3-diene with a carboxylic acid and oxygen in the presence of a catalyst containing palladium or platinum.

EXAMPLE 1

200 g of an 11% strength by weight solution of peracetic acid in glacial acetic acid are added to a solution of 46 g of 2-methyl-1,4-diacetoxybuta-1,3-diene in 420 g of glacial acetic acid at 95°±2° C. in the course of one hour, while stirring. Stirring is continued for a further 30 minutes at this temperature, after which unreacted peracetic acid can no longer be detected in the reaction mixture. The acetic acid is substantially stripped off in a rotary evaporator under about 20 mbar. The residue is fractionally distilled to give 38.1 g (76%, based on 2-methyl-1,4-diacetoxybuta-1,3-diene employed) of 2-methyl-4,4-diacetoxybut-2-enal of boiling point 94°–96° C./0.6 mbar, $n_D^{20} = 1.4562$.

EXAMPLE 2

240 g/hour of glacial acetic acid containing 5% by weight of 2-methyl-1,4-diacetoxybuta-1,3-diene, and 4 l (S.T.B.)/hour of oxygen, are introduced, at an internal temperature of 95°±2° C., into a reactor which has a free volume of 0.4 liter and is equipped with a blade stirrer (1,000 rpm). The pressure in the reactor is kept at 10 bar by forcing in oxygen. 1,157 g of 2-methyl-1,4-diacetoxybuta-1,3-diene are introduced in the course of 96 hours. The glacial acetic acid is substantially stripped off, in a rotary evaporator under about 20 mbar, from the 23.6 kg of reacted mixture obtained, and the residue is fractionally distilled over a column which has a length of 50 cm and a diameter of 3 cm and is filled with glass rings, to give 760 g (60%, based on 2-methyl-1,4-diacetoxybuta-1,31-diene employed) of 2-methyl-4,4-diacetoxybut-2-enal of boiling point 90°–92° C./0.5 mbar, $n_D^{20} = 1.4578$.

According to the $^1$H-NMR spectrum (CDCl$_3$), the distillate no longer contains any starting material, but comprises the trans-isomer together with not more than 10% of cis-2-methyl-4,4-diacetoxybut-2-enal.

EXAMPLE 3

6.8 g of 50% strength by weight hydrogen peroxide are added to a solution of 18.4 g of 2-methyl-1,4-diacetoxybuta-1,3-diene in 200 g of glacial acetic acid at 25°±2° C. in the course of 15 minutes, and the reaction mixture is heated to 95°±2° C. and stirred at this temperature for 2 hours. The glacial acetc acid is stripped off in a rotary evaporator at a bath temperature of 50° C. and under 25 mbar, after which the residue is fractionally distilled to give 11 g (55%, based on 2-methyl-1,4-diacetoxybuta-1,3-diene employed) of 2-methyl-4,4-diacetoxybut-2-enal of boiling point 90°–93° C./0.6 mbar, $n_D^{20}=1.4598$.

EXAMPLE 4

21.3 g of tert.-butyl hydroperoxide (84.4% strength by weight) in 180 g of glacial acetic acid are added to a solution of 36.8 g of 2-methyl-1,4-diacetoxybuta-1,3-diene in 300 g of glacial acetic acid at room temperature, while stirring. The mixture is then heated to 95° C. and stirred at this temperature for 4.5 hours. The glacial acetic acid is stripped off in a rotary evaporator, after which the residue is fractionally distilled to give 18.7 g of distillate of boiling point 92°–100° C./1 mbar, $n_D^{20}=1.4802$, which, according to the $^1$H-NMR spectrum (CDCl$_3$), comprises about 60% by weight of 2-methyl-4,4-diacetoxybut-2-enal and about 40% by weight of unreacted 2-methyl-1,4-diacetoxybuta-1,3-diene.

We claim:

1. A process for the preparation of a 2-alkyl-4,4-diacyloxybut-2-enal of the formula

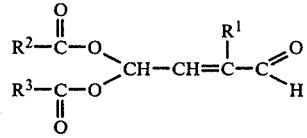

where R$^1$ is alkyl of 1 to 5 carbon atoms and R$^2$ and R$^3$ are each hydrogen, an aliphatic radical of 1 to 15 carbon atom, a cycloaliphatic radical of 5 to 7 carbon atoms or an aromatic radical, wherein a 2-alkyl-1,4-diacyloxybuta-1,3-diene of the formula

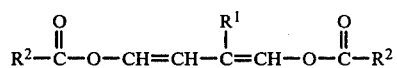

where R$^1$ and R$^2$ have the above meanings, is reacted with oxygen or an oxygen, donor, in the presence of a carboxylic acid of the formula

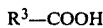

where R$^3$ has the above meanings.

2. A process as claimed in claim 1, wherein from 1 to 80 moles of the carboxylic acid of the formula III and from 0.5 to 10 moles of oxygen or of the oxygen donor are employed per mole of the diene of the formula II.

3. A process as claimed in claim 1, wherein the reaction is carried out at from 0° to 200° C.

* * * * *